United States Patent [19]

Williams et al.

[11] 4,226,115
[45] Oct. 7, 1980

[54] REMOTE CONTROLLED AIR SAMPLER

[75] Inventors: Ralph E. Williams; Larry L. Brown, both of Denver; Robert P. Marchese, Lakewood; Philip A. Russell; James A. Armstrong, both of Denver, all of Colo.

[73] Assignee: The United States of America as represented by the Administrator of the United States Environmental Protection Agency, Washington, D.C.

[21] Appl. No.: 920,944

[22] Filed: Jun. 30, 1978

[51] Int. Cl.³ .................. G01W 1/08; G01N 15/06
[52] U.S. Cl. ................................. 73/28; 73/170 R
[58] Field of Search ............................. 73/28, 170

[56] References Cited

U.S. PATENT DOCUMENTS

| | | | |
|---|---|---|---|
| 2,033,851 | 3/1936 | Roth | 219/4 |
| 2,722,998 | 11/1956 | Hall | 73/28 |
| 3,059,470 | 10/1962 | Baldwin | 73/170 |
| 3,063,296 | 11/1962 | Huch et al. | 73/421.5 R |
| 3,295,359 | 1/1967 | Peck | 73/28 |
| 3,464,257 | 9/1969 | Schreiber | 73/28 |
| 3,540,261 | 11/1970 | Scoggins | 73/421.5 R |
| 3,554,005 | 1/1971 | Koblin | 73/170 |
| 3,707,869 | 1/1973 | Raynor | 73/28 |

FOREIGN PATENT DOCUMENTS 526711 of 1976 U.S.S.R. .................. 73/421

*Primary Examiner*—S. Clement Swisher
*Attorney, Agent, or Firm*—Thomas W. Cole

[57] ABSTRACT

A portable, remote controlled air sampler for measuring the solid, liquid, and gaseous emissions from sources such as a fossil fuel power plant, or ambient air. The sampler comprises a pump operated suction head movably mounted on a guide means for sucking a sample of air through a selected portion of an air filter strip, a motor operated translating means for translating the suction head along the guide means, and a radio operated, remote control system for selectively actuating the translating means and suction head. The preferred embodiment of the sampler is sufficiently lightweight to be suspended from a buoyant balloon six feet in diameter or less, or having a gas capacity of 115 cubic feet or less.

12 Claims, 4 Drawing Figures

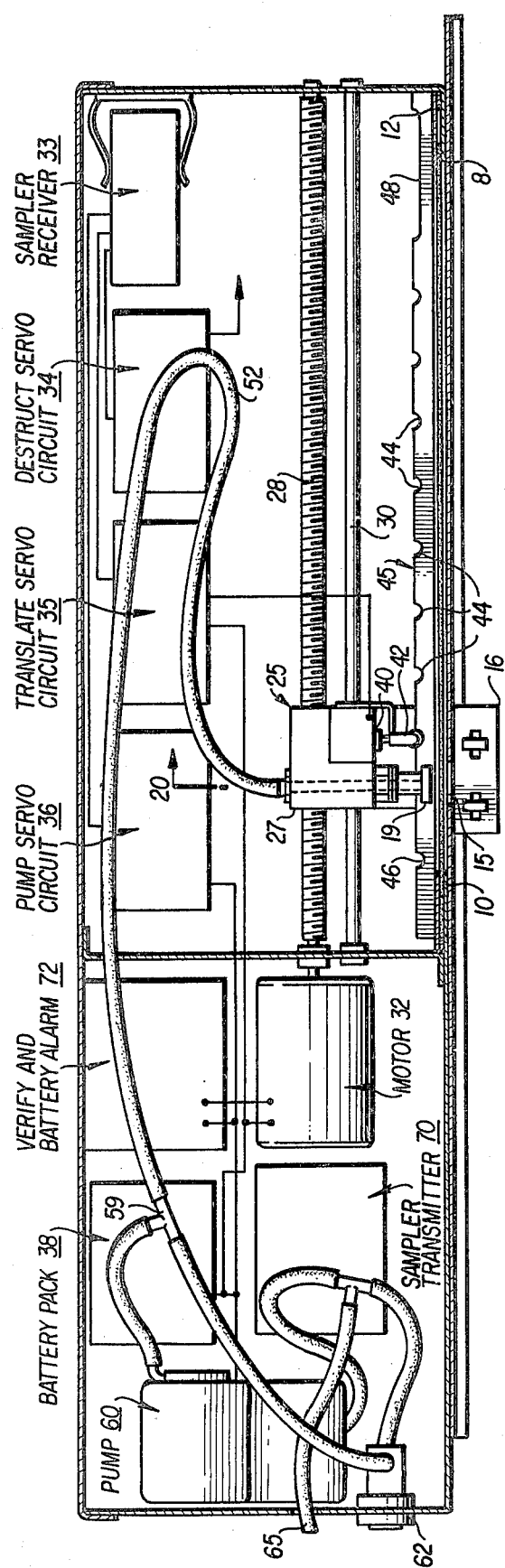
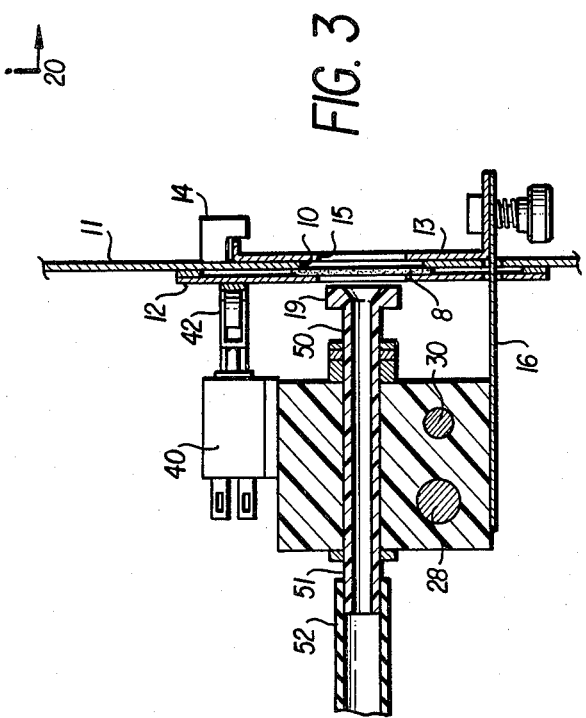
FIG. 2
FIG. 3

REMOTE CONTROLLED AIR SAMPLER

BACKGROUND OF THE INVENTION

The need for more versatile and portable air samplers has become more and more acute with the passage of an ever increasing number of anti-pollution laws by federal, state and local governments. In order to determine whether or not the type and concentration of contaminants emitted from a source of pollution fall within the standards defined in these recently promulgated laws, the need has arisen for a portable and versatile air sampling device capable of conveniently detecting and measuring the concentration of solid, liquid and gaseous contaminants present in emissions which are frequently located in areas of difficult accessibility, such as the tops of smokestacks of industrial installations.

None of the air samplers in the prior art are well adapted to fulfill this need. Schrieber et al U.S. Pat No. 3,464,257 discloses a remote controlled air sampler which is not portable and utilizes a bulky reel of filter paper of uniform sampling characteristics which is rhythmically fed past a stationary pneumatic feeder. Koblin U.S. Pat. No. 3,554,005, Scoggins U.S. Pat. No. 3,540,261, and Peck U.S. Pat. No. 3,295,359 illustrate samplers which are portable, but are controlled either by a timer means or manually. Finally, patents such as Huch et al U.S. Pat. No. 3,063,296 disclose air sampling systems light enough to be carried aloft by a buoyant balloon, but automatically actuated by an altimeter when the balloon rises to a predetermined height.

SUMMARY OF THE INVENTION

The invention basically relates to an air sampler adapted to be suspended by a balloon filled with buoyant gas comprising (1) a housing having a wall with an elongated aperture which is covered by an air filter strip, (2) a pump operated suction head within this housing which is movably mounted on a guide means, such as a linear track, for drawing an air sample through a portion of the filter strip, and (3) a suction head translating means for translating the suction head along the guide means, and (4) a remote control means for selectively actuating the suction head pump and translating means.

The air sampler of the invention is portable enough to be suspended by a buoyant balloon guided by a tether cable attached thereto, so that the operator of the sampler can conveniently guide the balloon-borne sampler into an area of difficult accessibility, such as the base of a smoke plume emitted by an industrial smokestack.

Furthermore, the preferred embodiment of the invention is capable of being suspended by a buoyant balloon six feet in diameter or less or having a gas capacity of 115 cubic feet or less, which is very advantageous since use of a larger diameter balloon would necessitate compliance with restrictive Federal Aviation Administration regulations such as, Part 101, March 1974, requiring lights for night operation, and forbidding usage within five miles of an airport or 500 feet of a cloud base.

Once guided into a selected sampling area, the invention is capable of operating by remote control in either a "discrete sample" mode or "continuous streak sample" mode.

In the "discrete sample" mode, the suction head is selectively translated to one of a plurality of discrete sampling positions corresponding to separate portions of the air filter strip. Operation in the "discrete sample" mode is particularly advantageous when the operator desires to take a series of samples at a variety of locations. Additionally, the different portions of the air filter strip which correspond to the different suction head sampling positions may be comprised of different filtration mediums adapted to sense different types of contaminants, so that the remote control means may be used to select an appropriate sampling medium.

In the "streak sample" mode, the suction head is continuously translated across the air filter strip as the suction head draws air, thereby forming a single sample streak across a portion of the air filter strip. The "streak sample" mode may be employed when the operator wishes to take a continuous air sample in one location over a selected period of time.

The use of a remote control has the advantage of allowing the operator to control when and how long the sampler is used, as well as whether to operate the device in the "discrete sample" or "continuous streak" mode. The use of a remote control has the added advantage of allowing the operator to temporarily deactuate the sampler in response to adverse temporary atmospheric conditions, such as when the wind might change the direction of a smoke plume being sampled, and then re-actuate the sampler upon cessation of the adverse condition.

Thus, the invention provides an advance over the prior art by providing an extremely versatile, remote controlled air sampler capable of being suspended by a buoyant balloon easily manipulated into an area of difficult accessibilty.

BRIEF DESCRIPTION OF THE DRAWINGS

FIG. 2 is a top plane view of the air sampler with the top of the housing removed;

FIG. 3 is a cross-sectional view of the sampling head taken along the line 20—20 in FIG. 2;

DETAILED DESCRIPTION OF THE PREFERRED EMBODIMENT

Figure 1:
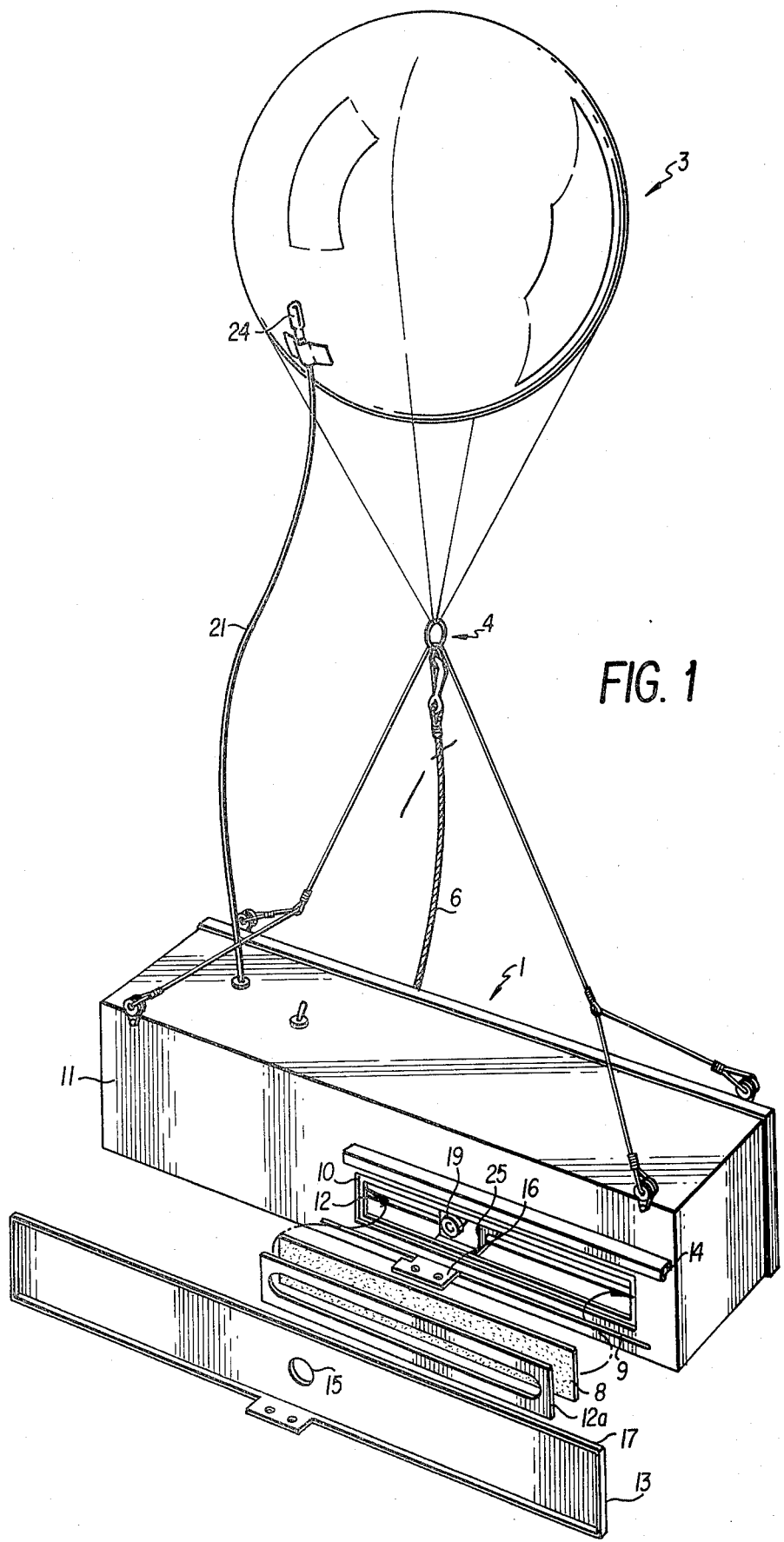
FIG. 1 is a front perspective view of the air sampler suspended from a balloon illustrating the air filter strip, and its masking and framing plates.

Referring now to the drawings, wherein like numbers refer to like components, FIG. 1 illustrates a front perspective view of the air sampler suspended by a balloon 3 (not drawn to scale) filled with a buoyant gas which is preferably helium, for reasons which will become apparent later. The balloon 3 is attached to the housing 1 of the sampler by means of an assembly 4 to which a guide means comprising a tether rope 6 is fastened.

The exploded portion of FIG. 1 illustrates an elongated aperture 10 in the front wall 11 of housing 1, over which an air filter strip 8 is mounted, and held in place by a thin slotted metal plate holder 12a. Filter strip 8 may be any filter material which collects airborne particulates, droplets or gases when an air pump sucks air through it. Further, the filter strip 8 may be comprised of composite of different types of filtration material corresponding to different sampling positions of the sampling head, thereby giving the operator the equipment of a choice of filters to use when the device is operated in the "discrete sample" mode. In the preferred embodiment, the filter strip 8 and holder 12a are mounted over the elongated aperture 10 and held in place by means of a filter framing plate 12 attached to the inside of housing wall 11. A filter cover plate 13 having an aperture 15 in registry with nozzle 19 of the suction head 25 is slidably engaged to a filter cover plate guide means 14 by means of a flange 17 extending outwardly from the top of cover plate 13 which is received in a complementary groove (shown in FIG. 2) formed from an overhanging shoulder of guide means 14. The filter cover plate 13 is movably connected to suction head 25 by means of a plate 16 which passes through a lengthwise slot 9 in housing wall 11 located just under the elongated aperture 10, so that the filter cover plate moves from side to side along with suction head 25 with suction nozzle 19 in registration with aperture 15.

Thus, filter cover plate 13 protects all of air filter strip 8 from exposure to the outside atmosphere except that portion exposed by aperture 15 through which air nozzle 19 sucks an air sample.

Also illustrated in FIG. 1 is a balloon destruct mechanism 24 which may be used to burn a hole in balloon 3 to return the sampler to earth should tether rope 6 become disconnected from winch assembly 4. Destruct mechanism 24 may contain either a flashbulb or small explosive which is electrically actuated through wire 21 by a destruct servo (shown in FIGS. 2 and 4) within housing 1. Since the destruct mechanism employs the use of heat, it is apparent that a non-flammable buoyant gas, such as helium, is preferable to a flammable buoyant gas, like hydrogen, since the use of the latter type could result in the destruction of the sampler.

FIG. 2 illustrates the operation of the mechanical system of the sampler. Suction head 25 generally comprises a block 27 having a threaded bore through which a leadscrew 28 passes through, and a smooth bore through which a block guide means, such as linear track 30, passes through. The block, leadscrew and track are all preferably constructed of a strong, lightweight materials such as nylon in order to minimize the weight of the sampler.

The leadscrew 28 is coupled to an electric motor 32 in a conventional manner. When the translate servo circuit 35 actuates electric motor 32 by closing the circuit between battery pack 38 and the motor, leadscrew 28 rotates, thereby translating sampling head 25 along leadscrew 28 in much the same fashion as a "riding nut". Linear track 30 serves both to guide air nozzle 19 of suction head 25 across a lengthwise portion of air filter strip 8, and to prevent suction head 25 from rotating along with leadscrew 28 when motor 32 is actuated.

FIGS. 2 and 3 generally illustrate the pneumatic system of the sampler. Nozzle 19 is integrally connected to a conduit 50 which passes completely through block 27 and forms a nipple 51 which projects from the back of the block as shown. Nipple 51 is pneumatically connected to air pump 60 by means of flexible tubing section 52. In the preferred embodiment air pump 60 comprises a stripped down Unico Micronaire II, Model 3900-10, although a number of other lightweight, miniature air pumps would be equally suitable. Tubing section 52 is connected to a T-joint 59, which in turn is connected to both the pump 60 and a flow adjust 62 through other suitable tubing sections as shown. Pump 60 is in turn pneumatically connected to a miniature ball-type flowmeter 65, which measures the amount of air drawn through suction nozzle 19 by pump 60.

The remote control of the sampler is basically comprised of a mechanical system working in conjunction with an electronic system.

With reference again to FIG. 2 and the mechanical system of the remote control, suction head 25 has mounted thereon a microswitch 40 having an extended actuating element 42 which engages an indexing bar 45 having a plurality of indentations 44, which correspond to pre-selected sampling positions for suction head 25. When the sampler is operated in the "discrete sample" mode, microswitch 40 serves to deactuate motor 32 whenever extended actuating element 42 is received into one of said indentations 44, thereby positioning suction head 25 over a discrete section of filter strip 8.

Figure 4:
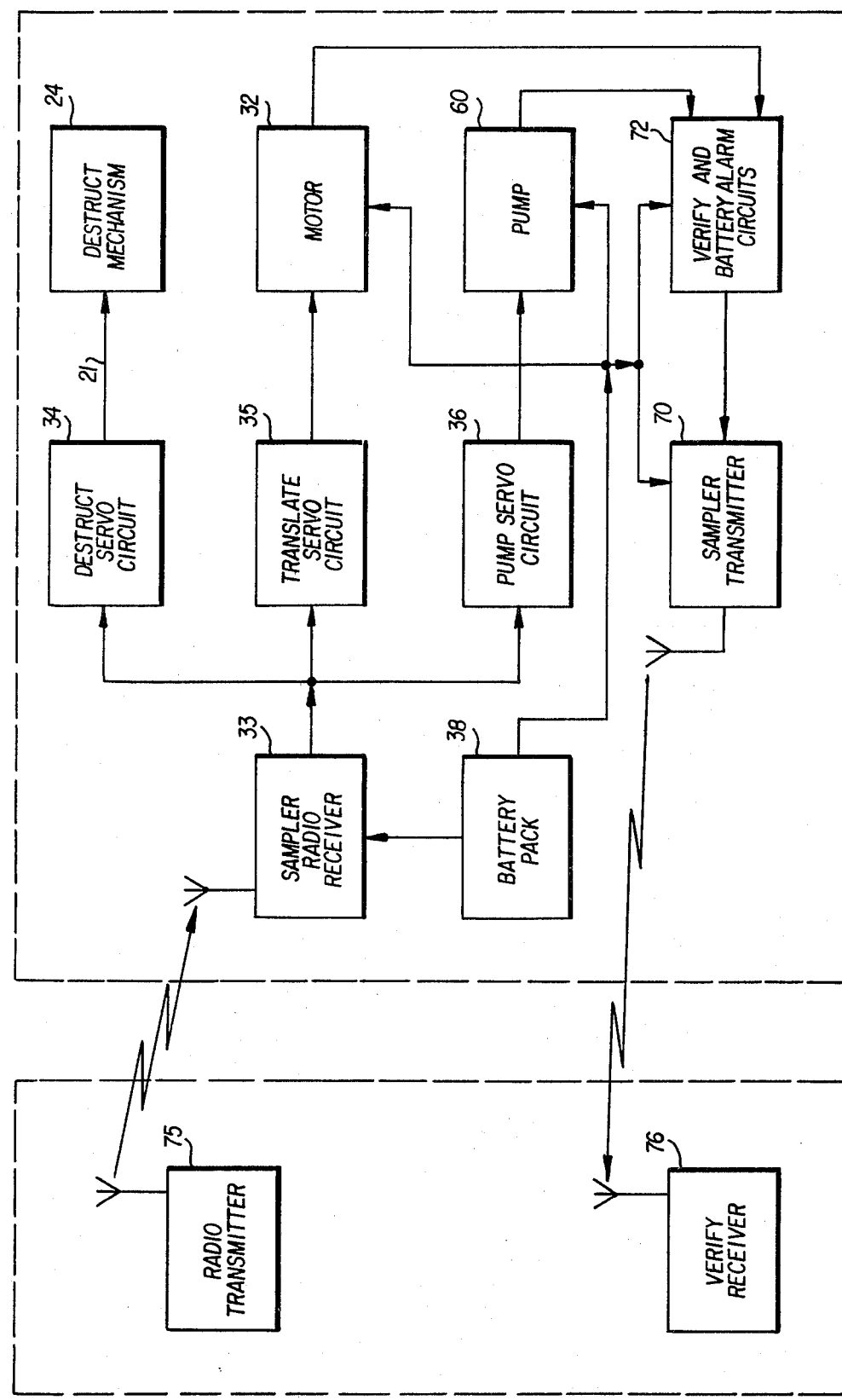
FIG. 4 is an electronic block diagram of the radio operated, remote control of the sampler.

The electronic system of the remote control system is illustrated by FIGS. 2 and 4. The sampler contains a radio receiver 33 for receiving radio command signals transmitted by the sampler operator via radio transmitter 75. The radio receiver is electrically connected to a destruct servo circuit 34, a translate servo circuit 35, and a pump servo circuit 36 as indicated. In the preferred embodiment, the radio receiver 33 is a Futaba FP-R3F three channel receiver, and each of the three servo circuits is a Futaba FP-S6 IC servo, each of which responds to one of the three channels of the receiver. Of course, any small, lightweight servo control could also be used.

The destruct servo circuit 34 is connected to destruct mechanism 24 by way of cable 21, and serves to actuate destruct mechanism 24 upon command.

The translate servo circuit 35 is connected to motor 32, and controls the actuation thereof, while microswitch 40 deactuates the motor as previously discussed. Motor 32 is connected to both the battery pack 38 (which may be a yardney silver cell, Model LRI-5) and the verify and battery alarm circuit 72. When the sampler is operated in the "discrete sample" mode of operation, the verify and battery alarm circuit 72 senses when motor 32 has translated suction head 25 into a new sampling position, and generates a signal verifying such. This signal is in turn received by a transmitter 70 located within the housing of the sampler, which broadcasts a signal down to the verify receiver 76, thus informing the operator that the suction head has in fact been translated into a new sampling position in accordance with the radio command signal transmitted by transmitter 75.

Pump servo circuit 36 is connected to pump 60 which in turn is connected to both the battery pack 38 and the verify and battery alarm circuit 72. When pump servo circuit 36 actuates pump 60 in response to servo control signals received from radio receiver 33, the verify and battery alarm circuit 72 senses that the pump has been actuated, and transmits a pump actuation verification signal to transmitter 70, which in turn transmits this information to receiver 76 in the same fashion as previously described with the motor 32. Additionally, it should be noted that circuit 72 constantly senses the power output of battery pack 38, and generates a "weak battery" signal which in turn is transmitted via transmitter 70 to the operator, thus informing him when battery pack 38 is in a weak condition.

OPERATION OF THE PREFERRED EMBODIMENT

First, the operator of the sampler guides the sampler into the desired sampling area via tether rope 6. At the beginning of the operation, suction head 25 is in an inactive position located at the far left of indexing bar 45 of FIG. 2, with extended actuating element 42 of microswitch 40 received in indentation 46 of the indexing bar. In this position, all of filter strip 8 is covered by the filter cover plate 13. The operator then transmits a translate command via transmitter 75 to receiver 33, which in turn causes translate servo circuit 35 to actuate motor 32 to translate suction head 25 into the first sampling position. Microswitch 40 deactuates motor 32 as soon as its extended actuating element is received in the next indentation of indexing bar 45, thus placing suction head 25 in the position illustrated in FIG. 2. Upon receiving a translate verification signal from sampler transmitter 70, the operator then actuates the sampler pump 60 by transmitting a pump actuation radio command via transmitter 75. The sampler then transmits a pump verification signal as previously described, via transmitter 70. The operator then allows the pump to draw a sufficient sample of air through the portion of air filter strip 8 adjacent to suction nozzle 19 in this first sampling position of suction head 25. After a sufficient sample has been taken, the process is repeated until eight separate samples have been taken corresponding to the eight sampling positions of suction head 25 on indexing bar 45. Of course, any number of samples can be taken by notching indentations 44 on a new indexing bar 45. The suction head 25 is then translated to rest position 48 on indexing bar 45, and filter cover plate 13 again covers all of air filter strip 8, protecting it from further exposure to air. The sampler is then taken down, and the air filter strip 8 is then removed for analysis.

The preceding description assumes that the sampler is operated in the "discrete sample" mode. When a continuous streak sample is desired, the operator merely continuously activates transmitter 75. An alternate method is to inactivate microswitch 40, but a stop microswitch is needed at the rest position 48. Once motor 32 is actuated with the extended actuating element 42 in this position, the suction head 25 will continue to travel along track 30 until it reaches rest position 48.

It should be noted that the remote control of the sampler may also be used to choose a particular filter medium when air filter strip 8 is comprised of a series of contiguous filtration meduims such that a different filter is associated with one or more of the various sampling positions. In this case, the operator notes the sampling position associated with the particular filtration medium he desires to use. He then positions suction head 25 at that particular sampling position by sequentially broadcasting an appropriate number of translate commands via transmitter 75. Motor 32 is a reversable D.C. motor, and the invention contemplates that servo translate circuit 35 has the capacity to selectively reverse the polarity of the power input to motor 32 from battery pack 38, so suction head 25 may be selectively placed from any position along track 30 to any one of the eight sampling positions.

Thus, the operation of an extremely reliable, portable and versatile air sampler has been described. The simple design of the sampler's mechanical system in combination with the fail safe, verification features of the remote control system make it very reliable, and lightweight enough to be suspended from a buoyant balloon six feet in diameter or less, or having a gas capacity of 115 cubic feet or less. Because many of the components are mass produced and readily available, the sampler of the invention is very inexpensive to build. Finally, the use of a filter strip and movable suction head, in combination with the remote control system, renders the sampler extremely versatile since different filtration mediums may be chosen by remote control.

The device is not restricted to use in a balloon, but may serve as any remote controlled system.

What is claimed is:

1. A remote controlled air sampler comprising:
   (a) a housing having a wall with an elongated aperture,
   (b) an air filter strip more extensive than said aperture mounted over said aperture,
   (c) a guide means mounted within said housing,
   (d) a suction head within said housing movably engaged to said guide means for sucking a sample of air through a portion of said air filter strip,
   (e) a suction head translating means operatively engaged to said suction head for translating said suction head along said guide means;
   (f) an air pump in fluid communication with said suction head for drawing a sample of air through said suction head, and
   (g) a radio operated, remote control means for selectively actuating said suction head translating means and said air pump in response to radio signals, whereby an air sample is drawn through a portion of said air filter means.

2. The air sampler of claim 1 wherein said suction head translating means includes a motor.

3. The air sampler of claim 2 wherein said radio operated, remote control means further includes
   (a) a radio receiver for generating servo control signals in response to said radio signals, and
   (b) a translate servo circuit electrically connected to said radio receiver for actuating said motor in response to said servo control signals.

4. The air sampler of claim 3 wherein said radio operated, remote control means further includes a pump servo circuit electrically connected to said radio receiver for actuating said pump in response to said servo control signals.

5. The air sampler of claim 4 wherein said radio operated, remote control means further includes
   (a) a microswitch means electrically connected to said translate servo circuit and mounted on said suction head for transmitting a motor deactuation signal to said translate servo circuit, said microswitch means including an extended actuating element,
   (b) an indexing bar mounted within said housing, and
   (c) a plurality of indentations in said indexing bar for receiving said extended actuating element of said microswitch means, each indentation corresponding to a sampling position of said suction head over a separate and discrete portion of said air filter strip, whereby said microswitch means is actuated to transmit a motor deactuation signal to said translate servo circuit when said suction head is in registry with one of said sampling positions.

6. The air sampler of claim 5 wherein said air filter strip comprises a plurality of different filtration mediums, each of which corresponds to one of said suction head sampling positions.

7. The air sampler of claim 6 further including a flow measuring means in fluid communication with said air pump for measuring the amount of air sucked through said selected portion of said air filter means through said suction head.

8. A remote controlled air sampler comprising:

(a) a housing having a wall with an elongated aperture, and
(b) an air filter strip more extensive than said aperture mounted over said aperture,
(c) a linear track mounted within said housing,
(d) a suction head within said housing movably mounted on said linear track for sucking a sample of air through a discrete portion of said air filter strip,
(e) a lead screw mounted within said housing and operatively engaged to said suction head for translating said suction head along said track into one of a plurality of sampling positions, each corresponding to a discrete portion of said air filter strip;
(f) a motor coupled to said lead screw for operatively turning said lead screw;
(g) an air pump in fluid communication with said suction head for drawing a sample of air through said suction head;
(h) a flow measuring means in fluid communication with said air pump for measuring the amount of air sucked through said selected portion of said air filter strip by said suction head, and
(i) a radio operated, remote control means for selectively actuating said motor to translate said suction head into registry with one of said plurality of sampling positions and for selectively actuating said air pump to draw a sample of air through said suction head in response to radio signals, whereby an air sample is drawn through a selected portion of said air filter means.

9. The air sampler of claim 8 wherein said radio operated, remote control means further includes (a) a radio receiver for generating servo control signals in response to said radio signals, and
(b) a translate servo circuit electrically connected to said radio receiver for actuating said motor in response to said servo control signals.

10. The air sampler of claim 9 wherein said radio operated, remote control means further includes a pump servo circuit electrically connected to said radio receiver for actuating said pump in response to said servo control signals.

11. The air sampler of claim 10 wherein said radio operated, remote control means further includes
(a) a microswitch means electrically connected to said translate servo circuit and mounted on said suction head for transmitting a motor deactuation signal to said translate servo circuit, said microswitch means including an extended actuating element,
(b) an indexing bar, and
(c) a plurality of indentations in said indexing bar for receiving said extended actuating element of said microswitch means, each indentation corresponding to one of said plurality of sampling positions of said suction head, whereby said microswitch means is actuated to transmit said motor deactuation signal to said translate servo circuit when said suction head is in registry with one of said sampling positions.

12. The air sampler of claim 11 wherein said air filter strip comprises a plurality of different filtration mediums, each of which corresponds to one of said suction head sampling positions.

* * * * *